(12) United States Patent
McCarthy et al.

(10) Patent No.: US 8,105,364 B2
(45) Date of Patent: Jan. 31, 2012

(54) SYSTEMS, DEVICES AND METHODS FOR STABILIZATION OF THE SPINAL COLUMN

(75) Inventors: Richard McCarthy, Little Rock, AR (US); Christopher E Johnson, Germantown, TN (US); Rex W Armstrong, Cordova, TN (US)

(73) Assignee: Warsaw Orthopedic, Inc., Warsaw, IN (US)

(*) Notice: Subject to any disclaimer, the term of this patent is extended or adjusted under 35 U.S.C. 154(b) by 0 days.

(21) Appl. No.: 12/707,349

(22) Filed: Feb. 17, 2010

(65) Prior Publication Data

US 2010/0145390 A1 Jun. 10, 2010

Related U.S. Application Data

(62) Division of application No. 11/102,167, filed on Apr. 8, 2005, now Pat. No. 7,708,762.

(51) Int. Cl.
*A61B 17/88* (2006.01)

(52) U.S. Cl. .......... 606/279; 606/257; 606/267

(58) Field of Classification Search .......... 606/257–258, 606/264–267, 279
See application file for complete search history.

(56) References Cited

U.S. PATENT DOCUMENTS

| | | | |
|---|---|---|---|
| 4,611,581 A | 9/1986 | Steffee | |
| 4,655,199 A | 4/1987 | Steffee | |
| 5,562,663 A | 10/1996 | Wisnewski et al. | |
| 5,672,175 A * | 9/1997 | Martin | 606/86 A |
| 5,697,929 A | 12/1997 | Mellinger | |
| 5,797,911 A | 8/1998 | Sherman et al. | |
| 6,004,349 A | 12/1999 | Jackson | |
| 6,056,753 A | 5/2000 | Jackson | |
| 6,059,786 A | 5/2000 | Jackson | |
| 6,110,172 A | 8/2000 | Jackson | |
| 6,113,601 A | 9/2000 | Tatar | |
| 6,176,214 B1 | 1/2001 | Yamaguchi | |
| 6,193,719 B1 | 2/2001 | Gournay et al. | |
| 6,224,596 B1 | 5/2001 | Jackson | |

(Continued)

FOREIGN PATENT DOCUMENTS

DE 202 07 850 U1 10/2002

(Continued)

OTHER PUBLICATIONS

Wild, A. et al., A New Technique for the Surgical Management of Deformities in the Growing Spine, BlomedIzInIsche Technik, 2002, p. 270-271, Band 47, Heft 11.

(Continued)

*Primary Examiner* — Eduardo C Robert
*Assistant Examiner* — Julianna N Harvey

(57) ABSTRACT

A system for stabilization of the spinal column, including an elongate support member extending along an axis and a plurality of anchor members configured for anchoring to respective vertebrae. A first of the anchor members is engaged to the support member in a manner that substantially prevents axial movement of the support member relative to the first anchor member, and a second of the anchor members is engaged to the support member in a manner that allows substantially unconstrained axial movement of the support member relative to the second anchor member. In a further embodiment, a third of the anchor members is engaged to the support member in a manner that also allows substantially unconstrained axial movement of the support member relative to the third anchor member, with the second and third anchor members positioned on opposite sides of the first anchor member.

20 Claims, 4 Drawing Sheets

U.S. PATENT DOCUMENTS

| | | |
|---|---|---|
| 6,224,598 B1 | 5/2001 | Jackson |
| 6,287,308 B1 | 9/2001 | Betz et al. |
| 6,296,642 B1 | 10/2001 | Morrison et al. |
| 6,296,643 B1 | 10/2001 | Hopf et al. |
| 6,299,613 B1 | 10/2001 | Ogilvie et al. |
| 6,436,099 B1 | 8/2002 | Drewry et al. |
| 6,440,132 B1 | 8/2002 | Jackson |
| 6,440,137 B1 | 8/2002 | Horvath et al. |
| 6,454,768 B1 | 9/2002 | Jackson |
| 6,478,795 B1 | 11/2002 | Gournay et al. |
| 6,616,669 B2 | 9/2003 | Ogilvie et al. |
| 6,645,772 B1 | 11/2003 | Kirby et al. |
| 6,652,526 B1 | 11/2003 | Arafiles |
| 6,689,133 B2 | 2/2004 | Morrison et al. |
| 6,730,089 B2 | 5/2004 | Jackson |
| 6,783,527 B2 | 8/2004 | Drewry et al. |
| 2001/0049527 A1 * | 12/2001 | Cragg .............................. 606/61 |
| 2002/0116001 A1 | 8/2002 | Schafer et al. |
| 2003/0187434 A1 | 10/2003 | Lin |

FOREIGN PATENT DOCUMENTS

| | | |
|---|---|---|
| FR | 2 799 949 A1 | 4/2001 |

OTHER PUBLICATIONS

Klemme, W. R. et al., Spinal Instrumentation Without Fusion for Progressive Scoliosis in Young Children, Journal of Pediatric Orthopaedics, Dec. 1997, p. 734-742, vol. 17(6).

Allen, B.L Jr. ,et al., A Modified Harrington Technique for Scoliosis, Journal of Pediatric Orthopaedics Part B, 1998, p. 95-105, vol. 7, No. 2.

* cited by examiner

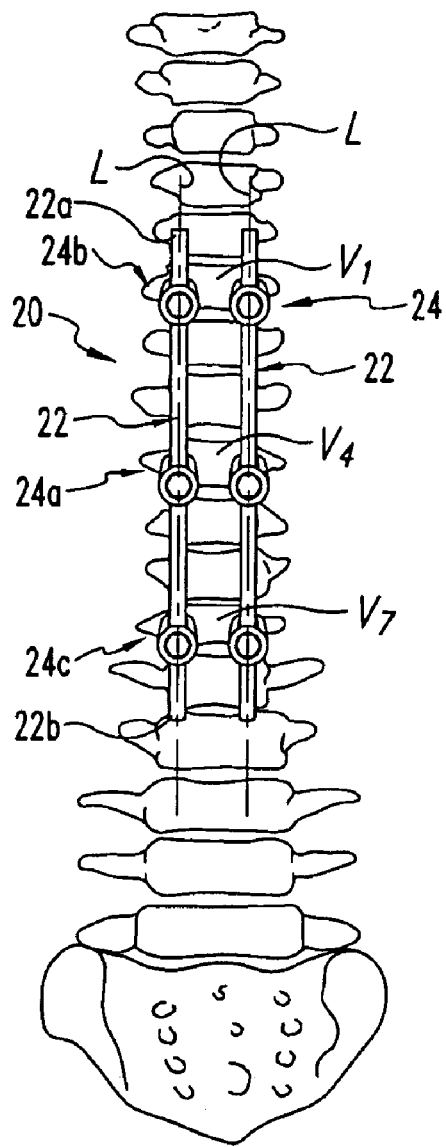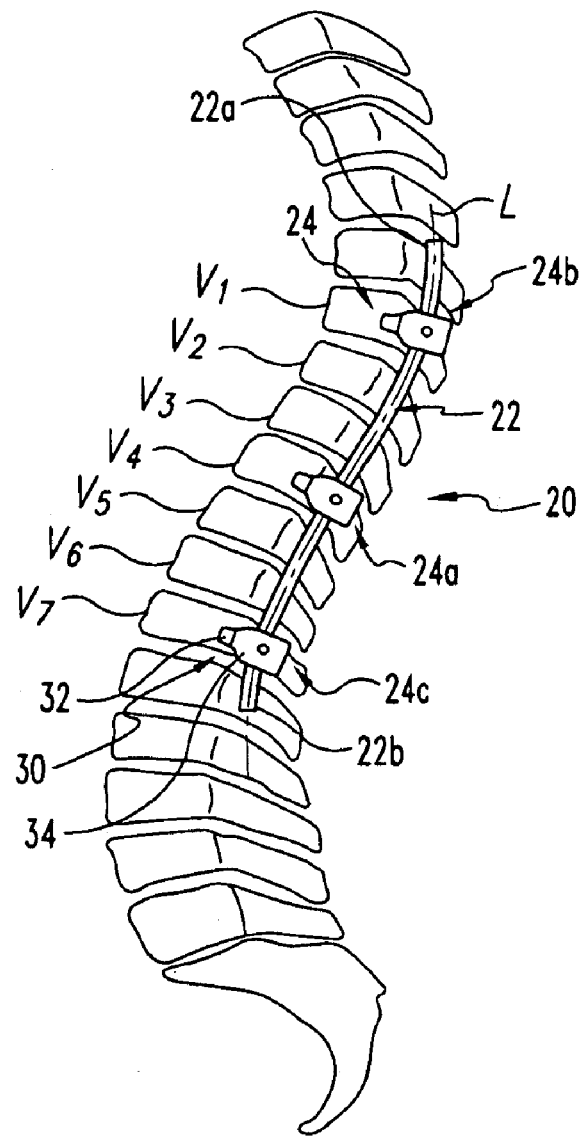
Fig. 1   Fig. 2

SYSTEMS, DEVICES AND METHODS FOR STABILIZATION OF THE SPINAL COLUMN

CROSS-REFERENCE TO RELATED APPLICATIONS

This application is a divisional of U.S. patent application Ser. No. 11/102,167 filed on Apr. 8, 2005, which is hereby incorporated herein by reference in its entirety.

FIELD OF THE INVENTION

The present invention generally relates to systems, devices and methods for treatment of the spinal column, and more particularly relates to systems, devices and methods for stabilizing a portion of the spinal column using one or more elongate members anchored to a number of vertebrae.

BACKGROUND

The spine is subject to various pathologies that compromise its load bearing and support capabilities. Such pathologies of the spine include, for example, degenerative diseases, the effects of tumors, and fractures and dislocations attributable to physical trauma. In the treatment of diseases, malformations or injuries affecting one or more spinal motion segments (which include two or more adjacent vertebrae and the disc tissue or disc space therebetween), and especially those affecting disc tissue, removal of some or all of a degenerated, ruptured or otherwise failing disc is sometimes required. It is also known that artificial discs, fusion implants, or other interbody devices can be placed into the disc space subsequent to removal of disc material. External stabilization of the spinal motion segments, alone or in combination with interbody devices, may be accomplished via attachment of one or more elongate plates, rods or other external stabilization devices to the spinal column.

Additionally, current operative methods for treating spinal deformities, particularly scoliosis, include correction of the spinal curvature via some form of internal fixation device, and fusion of the spine in the corrected state may be accomplished by the placement of bone graft between the adjacent vertebrae. Several instrumentation systems are available to correct and stabilize the spinal column while fusion occurs. Nonoperative methods also exist and may be used when applicable. These nonoperative methods include, for example, bracing and observation.

Patients with infantile or juvenile scoliosis who undergo curve stabilization via the use of subcutaneous rods are subject to multiple surgical procedures for lengthening and adjustment as they grow. As should be appreciated, it is generally preferable that the number of surgical procedures required for treatment of the spinal column be minimized. Additionally, anterior or posterior spinal fusion in a skeletally immature patient often results in loss of vertebral body height and girth. Another problem that sometimes arises is that some children are not physically able to tolerate the surgical procedures required for a definitive fusion procedure. Further, poor self-image may occur in adolescent patients who are externally braced for scoliosis. Moreover, curve stabilization with bracing is only successful in approximately 75% of patients.

While prior spinal stabilization and support systems are a step in the right direction, there remains room for additional improvements. For example, subsequent to implantation of prior stabilization systems, additional surgeries are sometimes required in order to adjust one or more components associated with the spinal construct. This is particularly true in instances involving growing patients, especially patients under the age of 10 years old, where the spinal construct must be periodically lengthened to accommodate for continued growth of the spinal column (e.g., to compensate for an increase in the distance between the spinal motion segments). In some instances, adjustments may be required every six months, thereby requiring multiple surgeries throughout the treatment process.

Thus, there is a general need in the industry to provided improved systems, devices and methods for stabilizing a portion of the spinal column using one or more elongate members. There is also a need to provide improved systems, devices and methods that reduce the number and/or frequency of adjustments to accommodate for continued growth of the patient's spinal column, particularly in pediatric patients having an immature spine. The present invention satisfies these and other needs and provides other benefits and advantages in a novel and unobvious manner.

SUMMARY

The present invention relates generally to systems, devices and methods for stabilizing a portion of the spinal column using one or more elongate members anchored to a number of vertebrae. While the actual nature of the invention covered herein can only be determined with reference to the claims appended hereto, certain forms of the invention that are characteristic of the preferred embodiments disclosed herein are described briefly as follows.

In one form of the present invention, a device is provided for attaching an elongate support member to the spinal column, including an anchor member having a bone engaging portion engageable to a vertebra and a receiver portion defining a passage configured to receive a portion of said support member, and a coupling member engaged with the receiver portion to retain the support member within the passage, with the receiver portion and the coupling member including structural features that cooperate to prevent the coupling member from compressing the support member against the receiver portion to thereby allow substantially unconstrained axial movement of the support member relative to the anchor member.

In another form of the present invention, a system for stabilization of the spinal column is provided, including an elongate support member extending along an axis and positioned along the spinal column, and a plurality of anchor members configured for anchoring to respective vertebrae, with a first of the anchor members engaged to the support member in a manner that substantially prevents axial movement of the support member relative to the first anchor member, and with a second of the anchor members engaged to the support member in a manner that allows substantially unconstrained axial movement of the support member relative to the second anchor member.

In another form of the present invention, a system is provided for stabilization of the spinal column, including an elongate support member extending along an axis and positioned along the spinal column, and a plurality of anchor members configured for anchoring to respective vertebrae. Each of the anchor members includes a bone engaging portion engageable to a vertebra and a receiver portion defining a passage configured to receive a portion of the support member therein. The system also includes a first coupling member engaged with a first of the anchor members to retain the support member within the passage, with the first coupling member cooperating with the first anchor member to compress the elongate member against the receiver portion of the first anchor member to substantially prevent axial movement of the support member relative to the first anchor member. The system further includes a second coupling member engaged with a second of the anchor members to retain the support member within the passage, with the second coupling member and the second anchor member including structural features that cooperate to prevent the second coupling member from compressing the support member against the receiver portion of the second anchor member to allow substantially unconstrained axial movement of the support member relative to the second anchor member.

In another form of the present invention, a method is provided for stabilizing the spinal column, including providing an elongate support member extending along an axis and providing a plurality of anchor members, anchoring a first of the anchor members to a first vertebra, anchoring a second of the anchor members to a second vertebra, engaging the first anchor member to the support member in a manner that substantially prevents axial movement of the support member relative to the first anchor member, and engaging the second anchor member to the support member in a manner that allows substantially unconstrained axial movement of the support member relative to the second anchor member.

It is one object of the present invention to provide improved systems, devices and methods for stabilizing a portion of the spinal column using one or more elongate members. Further objects, features, advantages, benefits, and aspects of the present invention will become apparent from the drawings and description contained herein.

BRIEF DESCRIPTION OF THE DRAWINGS

FIG. 1 is a posterior view of a spinal rod system according to one form of the present invention, as attached to a posterior aspect of the spinal column.

FIG. 2 is a lateral view of the spinal rod system illustrated in FIG. 1.

DESCRIPTION OF THE PREFERRED EMBODIMENTS

Figures 3, 4:
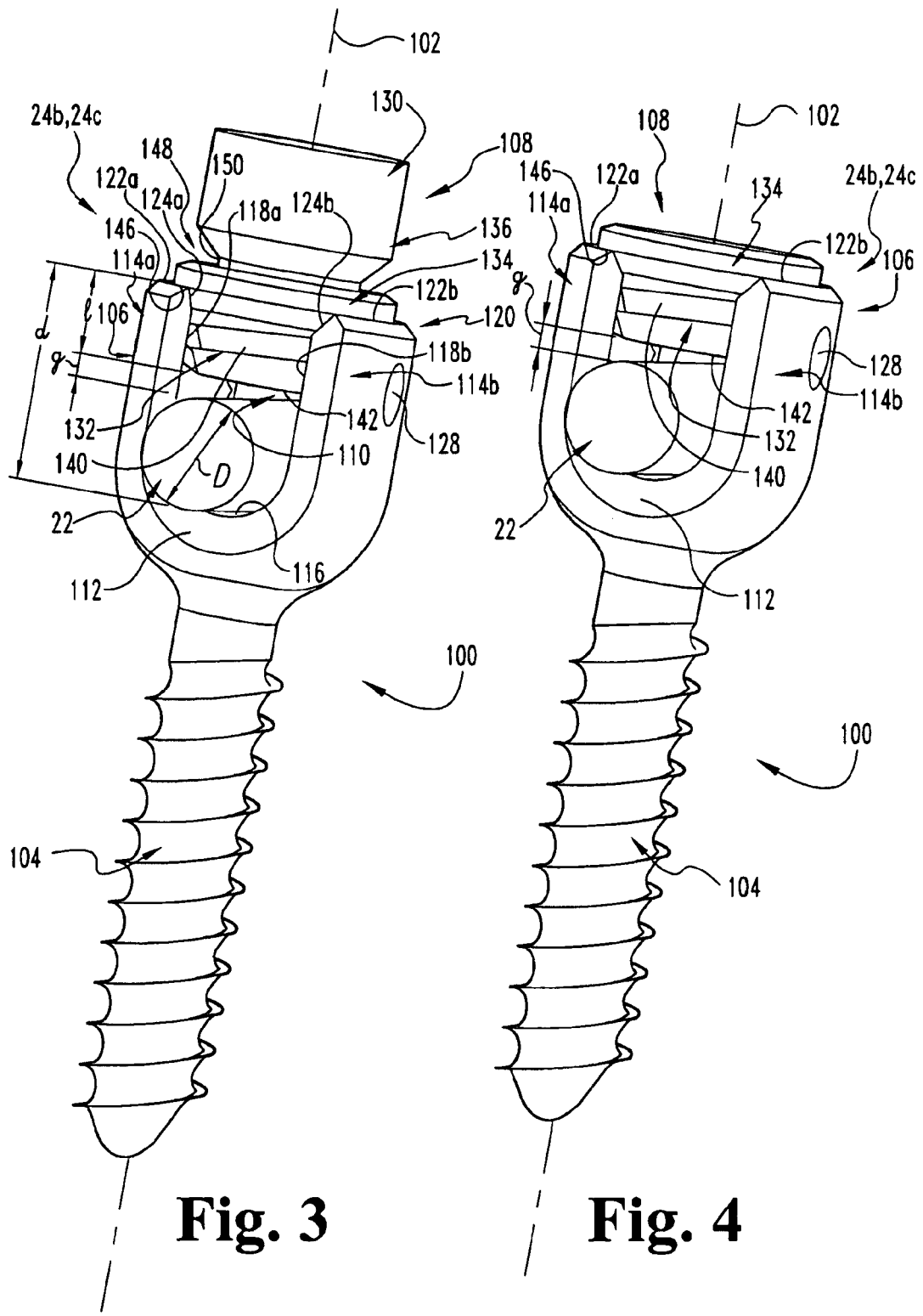
FIG. 3 is a side perspective view of one embodiment of a variable bone anchor assembly including a non-clamping setscrew for use in association with the spinal rod system illustrated in FIGS. 1 and 2.
FIG. 4 is a side perspective view of the variable bone anchor assembly illustrated in FIG. 4 with an upper portion of the non-clamping setscrew removed.

For the purposes of promoting an understanding of the principles of the invention, reference will now be made to the embodiments illustrated in the drawings and specific language will be used to describe the same. It will nevertheless be understood that no limitation on the scope of the invention is hereby intended, and that alterations and further modifications in the illustrated devices, and further applications of the principles of the invention as illustrated herein are contemplated as would normally occur to one skilled in the art to which the invention relates.

Referring to FIGS. 1 and 2, shown therein is a stabilization system 20 according to one form of the present invention for stabilizing at least a portion of the spinal column. In the illustrated embodiment, the stabilization system 20 extends across a plurality of vertebral levels including vertebrae $V_1$-$V_7$. However, it should be understood that the stabilization system 20 may extend across any number of vertebral levels including two or more vertebrae. Additionally, in the illustrated embodiment, the stabilization system 20 is attached to a posterior aspect of the spine. However, it should also be understood that the stabilization system 20 may be attached to other aspects of the spine, including anterior, antero-lateral, lateral, and/or postero-lateral aspects of the spine. Further, although the stabilization system 20 is illustrated as being used in association with the thoracic region of the spine, it should be understood that the stabilization system 20 may be utilized in other regions of the spine, including the cervical, lumbar, lumbo-sacral and sacral regions of the spine. It should also be understood that the stabilization system 20 can be used in association with fusion or fusionless treatment of the spine.

In the illustrated embodiment of the invention, the stabilization system 20 includes a pair of elongate members 22, each extending along a longitudinal axis L and engaged across a number of vertebral levels via a plurality of anchor members 24. However, it should be understood that the stabilization system 20 may utilize any number of elongate members 22, including a single elongate member or three or more elongate members. In the illustrated embodiment, the elongate members 22 are engaged to the spine by a first pair of anchor members 24a at a location at or near the coronal apex of the thoracic curve (e.g., adjacent vertebra $V_4$), by a second pair of anchor members 24b at a location one or more levels above the coronal apex (e.g., adjacent vertebra $V_1$), and by a third pair of anchor members 24c at a location one or more levels below the coronal apex (e.g., adjacent vertebra $V_7$). Engagement of one or more elongate members to the spine in this manner is sometimes referred to as the Shilla technique. Although the elongate members 22 are specifically illustrated as being specifically engaged to the vertebrae $V_1$, $V_4$ and $V_7$, it should be understood that the elongate members 22 may be engaged to each of the vertebrae $V_1$-$V_7$, to every other one of the vertebrae $V_1$-$V_7$, or to any number of the vertebrae $V_1$-$V_7$ via other layouts or attachment configurations.

According to one aspect of the present invention, the stabilization system 20 is configured to provide lateral stabilization or support to the portion of the spine being treated, while at the same time allowing for at least some degree of relative axial movement or motion between the vertebrae to which the elongate members 22 are engaged. In one embodiment, engagement between the elongate member 22 and at least one of the anchor members 24 is fixed or constrained so as to substantially prevent relative axial movement therebetween, and with engagement between the elongate member 22 and at least one of the anchor members 24 being variable or unconstrained so as to allow for relative axial movement therebetween. The combination of fixed and variable engagement between the elongate members 22 and the anchor members 24 provides at least some degree of relative axial movement or motion between the vertebrae to which the elongate members 22 are engaged (e.g., vertebrae $V_1$, $V_4$ and $V_7$). In one embodiment, the anchor members 24 that are variably engaged to the elongate member 22 allow for sliding movement of the anchor members 24 along an axial length of the elongate member 22 (e.g., in a direction generally along the sagittal plane), thereby allowing for relative axial movement or motion between the vertebrae to accommodate for continued growth of the patient's spine.

In the illustrated embodiment of the invention, the intermediate anchor members 24a are of the fixed or constrained type so as to substantially prevent relative axial movement between the elongate member 22 and the anchor members 24a, which likewise substantially prevents relative axial movement between the elongate member 22 and the vertebra $V_4$. Additionally, the outer anchor members 24b, 24c are each of the variable or unconstrained type so as to allow for relative axial movement between the elongate member 22 and the anchor members 24b, 24c. Such variable or unconstrained engagement between the elongate member 22 and the anchor members 24b, 24c likewise allows for relative axial movement between the elongate member 22 and the vertebrae $V_1$, $V_7$, which in turn allows for relative axial movement between each of the vertebrae $V_1$, $V_4$ and $V_7$ (and the intermediate vertebrae $V_1$, $V_2$ and $V_5$, $V_6$) to accommodate for growth of the patient's spine. Accordingly, the elongate members 22 provide lateral stabilization or support to the portion of the spine being treated, while at the same time allowing for substantially unrestricted or uninhibited axial movement to accommodate for growth of the patient's spine.

In one embodiment of the invention, each of the elongate members 22 is generally configured as an elongate tether, and more specifically as an elongate spinal rod. In the illustrated embodiment, the spinal rods 22 each have a generally circular outer cross section; however, other suitable cross sections are also contemplated as falling within the scope of the present invention including, for example, elliptical, triangular, rectangular, hexagonal or polygonal shapes and configurations, or any other suitable shape or configuration. In another embodiment of the invention, the elongate members 22 have a rigid or semi-rigid configuration suitable for providing a degree of lateral stabilization or support to the portion of the spinal column being treated. However, in other embodiments, the elongate members 22 may have a flexible or semi-flexible configuration and may exhibit resilient or semi-resilient characteristics.

Although the elongate members 22 are illustrated as having a rod configuration, it should be understood that the elongate members 22 may take on other configurations as well such as, for example, plates, cables, wires, artificial strands, artificial ligaments, springs, or other types of elongate members known to those of skill in the art that are suitable to stabilize and/or support at least a portion of the spine. In one embodiment, the elongate members 22 are formed of a metallic material such as, for example, titanium, a titanium alloy, stainless steel, a chrome-cobalt alloy, a shape-memory or superelastic material such as nitinol, or other suitable metallic materials know to those of skill in the art. In other embodiments, the elongate member 22 may be formed of a polymer such as, for example, polyester or polyethylene, or from a synthetic material.

In the illustrated embodiment of the invention, the anchor members 24 are configured as bone anchors 30 comprising a bone engaging portion 32 structurally configured for engagement with vertebral bone, and a receiver portion 34 structurally configured for engagement with one of the spinal rods 22. As will be set forth below in greater detail, in the illustrated embodiment, the anchor members are configured as bone screws. However, it should be understood that other types and configurations of anchor members are also contemplated as falling within the scope of the present invention including, for example, spinal hooks, staples, various types and configurations of connectors, or other types of anchor members known to those of skill in the art that are suitable for engaging one or more spinal rods 22 to the spinal column. In one embodiment, the anchor members 24 are formed of a metallic material such as, for example, titanium, a titanium alloy, stainless steel, a chrome-cobalt alloy, a shape-memory or superelastic material such as nitinol, or other suitable metallic materials know to those of skill in the art. In other embodiments, the anchor to members 24 may be formed of a polymer such as, for example, polyester or polyethylene, or from a synthetic material.

Referring to FIGS. 3 and 4, shown therein is one embodiment of anchor members 24b, 24c of the variable or unconstrained type which are configured to allow for axial movement relative to the spinal rod 22. In the illustrated embodiment, the anchor members 24b, 24c are configured as bone screws 100 extending along a longitudinal axis 102, and more specifically as pedicle screws. However, it should be understood that other types and configurations of bone screws are also contemplated for use in association with the present invention.

The bone screw 100 generally includes a threaded shaft portion 104 configured for engagement with bone, and a head portion 106 configured for engagement with one of the spinal rods 22. In the illustrated embodiment, the threaded shaft portion 104 and the head portion 106 are formed integral with one another so as to define a single-piece bone screw. However, in other embodiments of the invention, the threaded shaft portion 104 and the head portion 106 may be formed separately and subsequently engaged to one another so as to define an integral bone screw assembly. In the illustrated embodiment, the anchor members 24b, 24c also include a coupling member 108 configured to capture and retain the spinal rod 22 within the head portion 106 of the bone screw 100 in a variable or unconstrained manner so as to allow for relative axial movement between the spinal rod 22 and the bone screw 100, the purpose and details of which will be set forth below.

Although the shaft portion 104 is illustrated and described as defining external threads, it should be understood that the shaft portion 104 may alternatively define other features for anchoring to bone such as, for example, barbs, teeth, pivoting gulls, or other suitable anchoring features know to those of skill in the art. Additionally, in the illustrated embodiment, the head portion 106 defines a passage 110 extending transversely through the head portion 106 and sized and configured to receive one of the spinal rods 22 therein. In one embodiment, the passage 110 is defined by a base portion 112 and a pair of spaced apart arm portions 114a, 114b extending from the base portion 112. The transverse passage 110 is substantially U-shaped, with the base portion 112 defining a concave lower surface 116, and the arm portions 114a, 114b arranged substantially parallel to one another and define a pair of spaced apart side surfaces 118a, 118b. The transverse passage 110 is preferably configured to provide a relatively close fit between the elongate members 22 and the lower surface 116 and side surfaces 118a, 118b of the head portion 106, the purpose of which will be discussed below. Although a specific configuration of the head portion 106 has been illustrated and described herein, it should be understood that other types and configurations of screw head portions and other shapes and configurations of the transverse passage are also contemplated as falling within the scope of the present invention.

In the illustrated embodiment of the bone screw 100, the head portion 106 has an open upper end 120 in communication with the passage 110, with the ends of the arm portions 114a, 114b defining end surfaces 122a, 122b, respectively, adjacent the open upper end 120. The end surfaces 122a, 122b are offset from the lower surface 116 of the head portion 106, thereby providing the passage 110 with an overall depth d. Each of the arm portions 114a, 114b also defines a tapered surface 124a, 124b, respectively, extending between the side surfaces 118a, 118b and the end surfaces 122a, 122b. Additionally, at least the upper portions of the inner side surfaces 118a, 118b define internal threads (not shown), the purpose of which will be discussed below. The outer side surfaces of the arm portions 114a, 114b define indentations or recesses 128 sized and configured to receive corresponding portions of an instrument or tool therein (e.g., an insertion tool, a driver instrument, a compression instrument).

In the illustrated embodiment of the invention, the coupling member 108 is configured as a fastener or setscrew 130. In one embodiment, the setscrew 130 is of a non-clamping type that does not securely engage or compress against the elongate member 22 positioned within the head portion 106 of the bone screw 100, the details of which will be discussed below. However, it should be understood that other types and configurations of coupling members are also contemplated for use in association with the present invention for coupling the spinal rod 22 with the bone screw 100.

In one embodiment, the setscrew 130 generally includes a body portion 132, a flange portion 134, and a head portion 136. The body portion 132 of the setscrew 130 defines external threads 140 configured for threading engagement with the internal threads formed along the arm portions 114a, 114b of the bone screw head portion 106, and also defines a lower end surface 142 facing the lower surface 116 of the U-shaped passage 110 when the setscrew 130 is engaged between the arm portions 114a, 114b. The flange portion 134 of the setscrew 130 is sized larger than the body portion 132 so as to define a shoulder 146 that is offset from the lower end surface 142 of the setscrew 130, thereby providing the body portion 132 of the setscrew 130 with an overall length l. The head portion 136 of the setscrew 130 extends from the flange portion 134 and defines a tool engaging feature (not shown) for engagement with a corresponding portion of a driving tool for application of a rotary driving force to the setscrew 130. In one embodiment, the tool engaging feature comprises a recess configured to receive a corresponding projection of a driving tool therein. In a specific embodiment, the recess has a hexagonal configuration sized to receive a hexagonal-shaped end portion of a driving tool therein. However, it should be understood that the setscrew 130 may be provided with other types and configurations of tool engaging features that would be apparent to those of skill in the art.

In one embodiment, the head portion 136 is removably attached to the remainder of the setscrew 130 in such a manner as to allow selective separation of the head portion 136. In the illustrated embodiment, the head portion 136 is attached to the flange portion 134 by a region of reduced strength 148 to allow the head portion 136 to be fractured or broken off from the remainder of the setscrew 130 (see FIG. 4). In a specific embodiment, the region of reduced strength 148 is formed by a reduced cross-sectional area 150 adjacent the connection location between the head portion 136 and the flange portion 134. However, it should be understood that other features for allowing selective removal of the head portion 136 from the remainder of the setscrew 130 are also contemplated as falling within the scope of the present invention. It should also be understood that the in other embodiments of the invention the setscrew 130 need not necessarily include a removable head portion 136. Instead, one or more tool engaging features may be incorporated into the body portion 132 and/or the flange portion 134 for application of a rotary driving force to the setscrew 130.

Figures 5, 6:
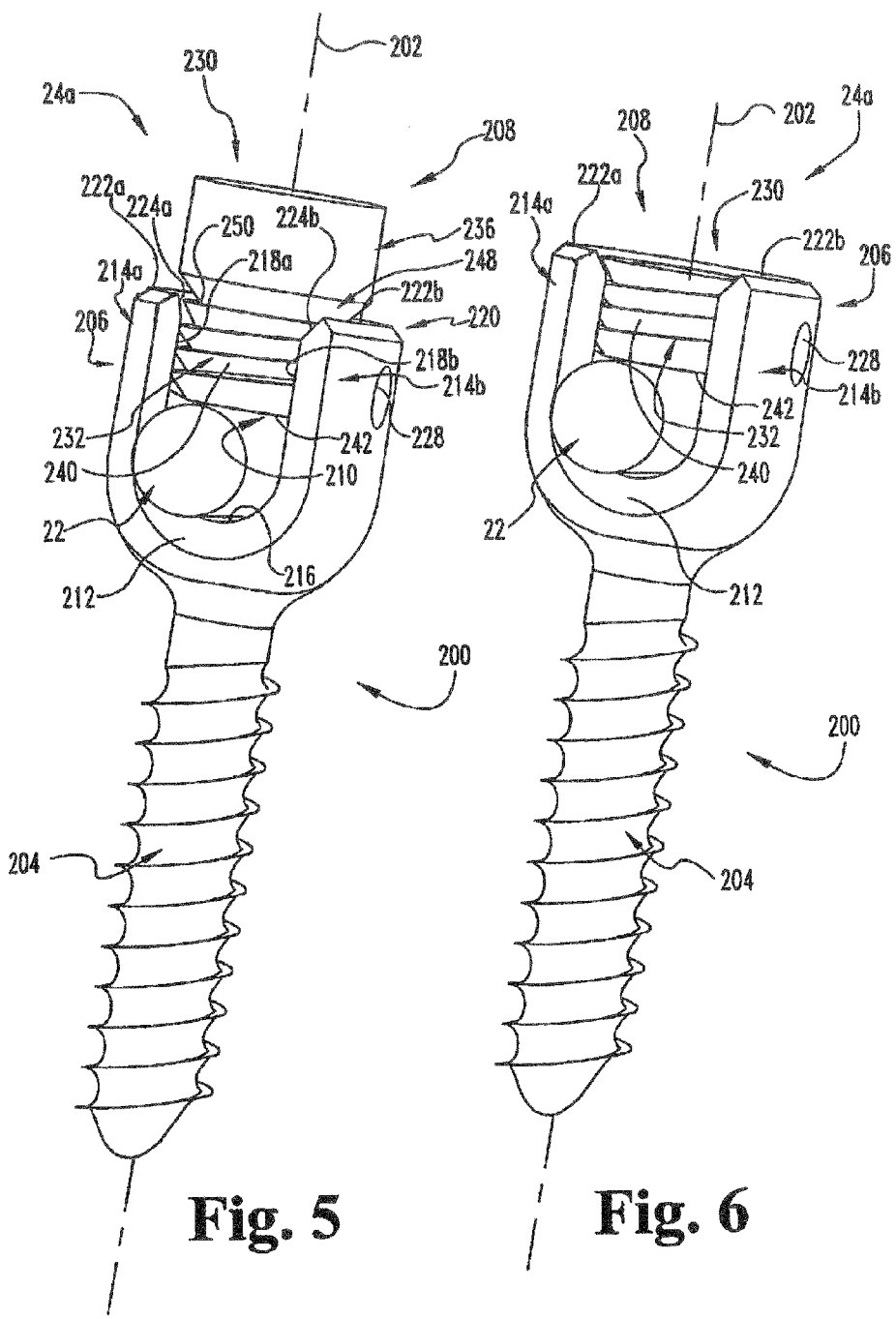
FIG. 5 is a side perspective view of one embodiment of a fixed bone anchor assembly including a clamping setscrew for use in association with the spinal rod system illustrated in FIGS. 1 and 2.
FIG. 6 is a side perspective view of the fixed bone anchor assembly illustrated in FIG. 5 with an upper portion of the clamping setscrew removed.

Referring to FIGS. 5 and 6, shown therein is one embodiment of the anchor member 24a of the fixed or constrained type which is configured to substantially prevent relative axial movement relative to the spinal rod 22. In the illustrated embodiment of the invention, the anchor member 24a is configured as a bone screw 200 extending along a longitudinal axis 202, and more specifically as a pedicle screw. In the illustrated embodiment, the bone screw 200 is configured identical to the bone screw 100 illustrated and described above. Accordingly, each of the features associated with the bone screw 200 need not be discussed in detail herein, it being understood that these features, as well as the additional embodiments discussed above with regard to the bone screw 100, also apply to the bone screw 200.

The bone screw 200 generally includes a threaded shaft portion 204 configured for engagement with bone, and a head portion 206 configured for engagement with one of the spinal rods 22. In the illustrated embodiment, the anchor member 24a also includes a coupling member 208 that is configured to capture and retain the spinal rod 22 within the head portion 206 of the one screw 200 in a fixed or constrained manner so as to substantially prevent relative axial movement between the elongate member 22 and the bone screw 200, the purpose and details of which will be set forth below. The head portion 206 defines a passage 210 extending transversely through the head portion 206 and sized and configured to receive one of the spinal rods 22 therein. In the illustrated embodiment, the passage 210 is defined by a base portion 212 and a pair of spaced apart arm portions 214a, 214b that extend from the base portion 212. In one embodiment, the transverse passage 210 is substantially U-shaped, with the base portion 212 defining a concave lower surface 216 and the arm portions 214a, 214b arranged substantially parallel to one another and defining a pair of spaced apart side surfaces 218a, 218b. The transverse passage 210 is preferably configured to provide a relatively close fit between the elongate members 22 and the lower surface 216 and side surfaces 218a, 218b of the head portion 206.

In the illustrated embodiment of the bone screw 200, the head portion 206 has an open upper end 220 in communication with the passage 210, with the ends of the arm portions 214a, 214b defining end surfaces 222a, 222b, respectively, adjacent the open upper end 220 of the head portion 206. Each of the arm portions 214a, 214b also defines a tapered surface 224a, 224b, respectively, extending between the side surfaces 218a, 218b and the end surfaces 222a, 222b. Additionally, at least the upper portions of the inner side surfaces 218a, 218b define internal threads (not shown). The outer side surfaces of the arm portions 214a, 214b define indentations or recesses 228 sized and configured to receive corresponding portions of an instrument or tool therein.

In the illustrated embodiment of the invention, the coupling member 208 is configured as a fastener or setscrew 230. In one embodiment, the setscrew 230 is of a clamping type that is capable of securely engaging or compressing against an elongate member 22 positioned within the head portion 206 of the bone screw 200. However, it should be understood that to other types and configurations of coupling members are also contemplated for use in association with the present invention for engaging the spinal rod 22 with the bone screw 200.

The setscrew 230 generally includes a body portion 232 and a head portion 236. The body portion 232 defines external threads 240 configured for threading engagement with the internal threads formed along the arm portions 214a, 214b, and also defines a lower end surface 242 facing the lower surface 216 of the U-shaped passage 210 when the setscrew 230 is engaged between the arm portions 214a, 214b. The head portion 236 of the setscrew 230 extends from the body portion 232 and defines a tool engaging feature (not shown) for engagement with a corresponding portion of a driving tool. In one embodiment, the head portion 236 is removably attached to the remainder of the setscrew in such a manner as to allow selective separation of the head portion 236. In the illustrated embodiment, the head portion 236 is attached to the body portion 232 by a region of reduced strength 248 to allow the head portion 236 to be fractured or broken off from the remainder of the setscrew 230 (see FIG. 6). In a specific embodiment, the region of reduced strength 248 is formed by a reduced cross-sectional area 250 adjacent the connection location between the head portion 236 and the body portion 232.

Having described the various features associated with the spinal rod 22 and the anchor members 24, reference will now be made to assembly of the stabilization system 20 and the interaction between the spinal rod 22 and the anchor members 24 accordingly to one embodiment of the invention. As indicated above, in one embodiment, the stabilization system 20 includes a pair of elongate spinal rods 22 engaged across a number of vertebral levels via a plurality of the anchor members 24. In the illustrated embodiment, an anchor member 24a of the fixed or constrained type (e.g., bone screw 200) is anchored to each side of the vertebra $V_4$, an anchor member 24b of the variable or unconstrained type (e.g., bone screw 100) is anchored to each side of the vertebra $V_1$, and an anchor member 24c of the variable or unconstrained type (e.g., bone screw 100) is anchored to each side of the vertebra $V_7$. However, as also indicated above, it should be understood that the anchor members may be anchored to any of the vertebrae via other layout arrangements or configurations.

Once the anchor members 24a-24c are properly anchored to the vertebrae and arranged such that the transverse passages 110, 210 are generally aligned with one another, an elongate member 22 (e.g., a spinal rod) is inserted into the generally aligned passages 110, 210 via the open upper ends 120, 220 of the head portions 106, 206. The tapered surfaces 124a, 124b and 224a, 224b adjacent the upper ends of the head portions aid insertion of the elongate member 22 into the transverse passages 110, 210. The elongate members 22 may be contoured or bent to facilitate correction of the spinal deformity and/or to accommodate for the curvature or anatomy of the spinal column. Notably, the end portions 22a, 22b of the elongate members 22 extend beyond the upper and lower anchor members 24b, 24c a significant distance to accommodate for future growth of the patient's spinal column, the details of which will be discussed below. In one embodiment of the invention, the end portions 22a, 22b of the elongate members 22 extend about one to two inches beyond the upper and lower anchor members 24b, 24c. However, other lengths of the end portions 22a, 22b are also contemplated.

Following insertion of the elongate members 22 into the transverse passages 210 of the anchor members 24a, a setscrew 230 of the clamping type is threadingly engaged between the arm portions 214a, 214b of each anchor member 24a. The setscrew 230 is axially advanced along the threads formed in the passage 210 until the setscrew 230 is tightly compressed against the elongate member 22 so as to securely clamp the elongate member 22 between the lower end surface 242 of the setscrew 230 and the lower engagement surface 216 of the bone screw 200, thereby substantially preventing relative movement between the elongate member 22 and the anchor member 24a. In other words, movement of the elongate member 22 is constrained relative to the anchor member 24a. The lower end surface 242 of the setscrew 230 may define surface features that function to aid in gripping the elongate member 20 including, for example, teeth, spikes, knurling, protrusions or other types of surface features know to those of skill in the art. Once the setscrew 230 is tightly compressed against the elongate member 22, exerting additional torque onto the setscrew 230 beyond a predetermined level will cause the head portion 236 to be sheared or broken off from the remainder of the setscrew 230 adjacent the region of reduced strength 248 (see FIG. 6). After the head portion 236 of the setscrew 230 is removed, the upper end of the body portion 232 will be substantially flush with the upper end surfaces 222a, 222b of the arm portions 214a, 214b.

Following insertion of the elongate members 22 into the transverse passages 110 of the anchor members 24b, 24c, a setscrew 130 of the nonclamping type is threadingly engaged between the arm portions 114a, 114b of each anchor member 24b, 24c. The setscrew 130 is axially advanced along the threads formed in the transverse passage 110 until the flange portion 134 is engaged against the upper end surfaces 122a, 122b of the head portion 106. Notably, the lower end surface 142 of the setscrew 130 is not compressed against the elongate member 22 when the shoulder 146 defined by the flange portion 134 is engaged against the upper end surfaces 122a, 122b of the head portion 106. Instead, a gap g exists between the lower end surface 142 of the setscrew 130 and the elongate member 22, thereby allowing for relative axial movement between the elongate member 22 and the anchor members 24b, 24c. In other words, movement of the elongate member 22 is unconstrained relative to the anchor members 24b, 24c. As should be appreciated, the gap g is formed by providing a setscrew 130 including a body portion 132 having a length l that is less than the difference between the depth d of the transverse passage 110 in the anchor head portion 106 and the diameter D of the elongate member 22. Once the flange portion 134 of the setscrew 130 is tightly compressed against the upper end surfaces 122a, 122b of the head portion 106, exerting additional torque onto the setscrew 130 beyond a predetermined level will cause the head portion 136 to be sheared or broken off from the remainder of the setscrew 130 adjacent the region of reduced strength 148 (see FIG. 4). After the head portion 136 of the setscrew 130 is removed, the only portion of the setscrew 130 extending beyond the upper end surfaces 122a, 122b of the arm portions 114a, 114b is the flange portion 134.

Figure 7:
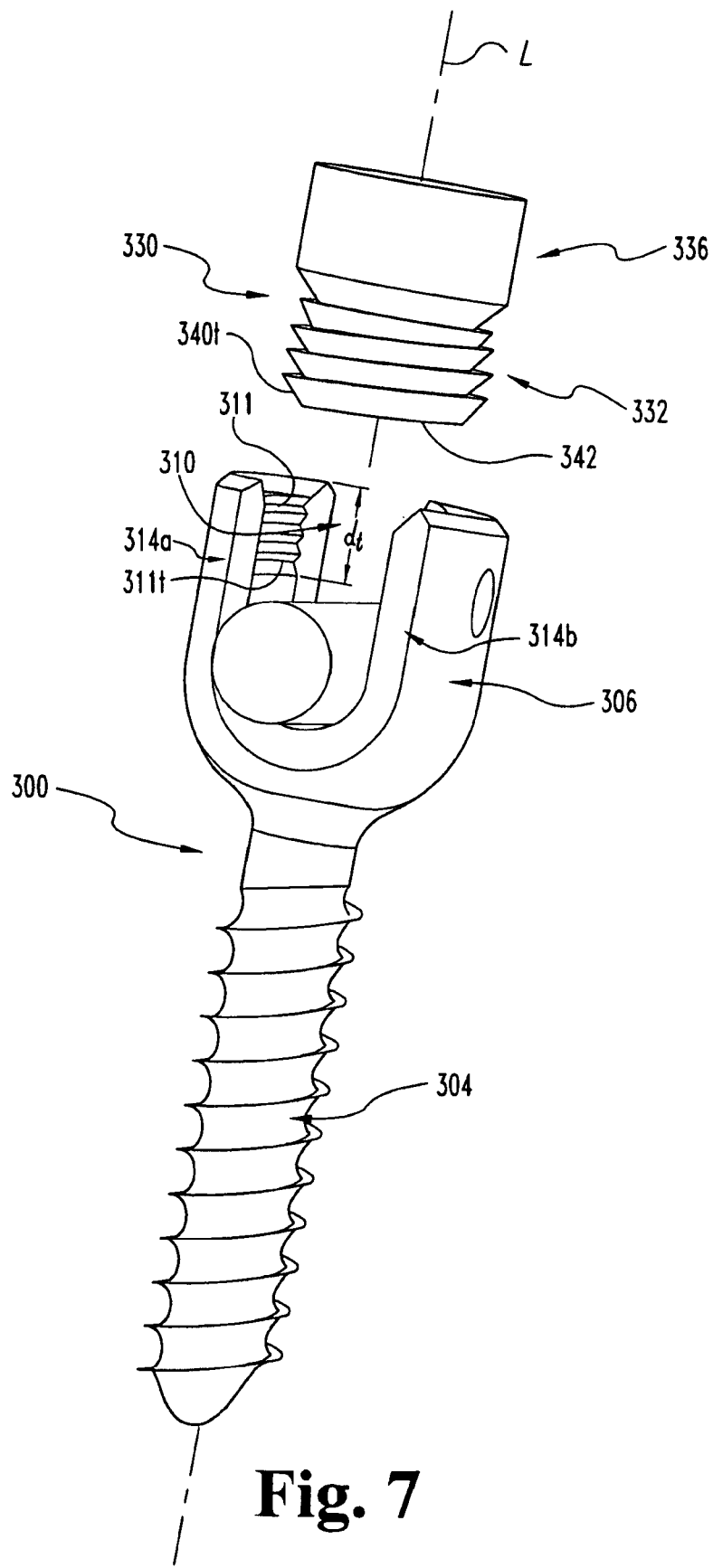
FIG. 7 is a side perspective view of another embodiment of a variable bone anchor assembly including a non-clamping setscrew for use in association with the spinal rod system illustrated in FIGS. 1 and 2.

Referring to FIG. 7, shown therein is another embodiment of the present invention including a bone anchor 300 and a setscrew 330 of the nonclamping type that may be threadingly engaged with the bone anchor 300 in a manner which avoids compression of the set screw 330 against an elongate member engaged with the bone anchor 300 to thereby permit axial movement of the elongate member relative to the bone anchor. In the illustrated embodiment, the bone anchor 300 comprises a bone screw including a threaded shaft portion 304 configured for engagement with bone, and a head portion 306 configured for engagement with a spinal rod in a manner similar to that illustrated and described above with regard to the bone screw 100. In virtually all respects, the bone screw 300 is configured identical to the bone screw 100, with the head portion 306 including arm portions 314a, 314b defining a transverse passage 310 therebetween, and with internal threads 311 formed along the interior side walls of the arm portions 314a, 314b for threading engagement with the body portion 332 of the set screw 330.

Notably, the set screw 330 does not include a flange portion that is engageable against upper end surfaces of the head portion 306 to prevent the set screw 330 from compressing against an elongate member positioned within the transverse passage 310. Instead, the internal threads 311 formed along the interior side walls of the arm portions 314a, 314b are limited to a thread depth $d_t$ such that the terminal or final internal thread $311_t$ is offset from the top of the spinal rod when the spinal rod is fully seated within the transverse passage 310 of the screw head portion 306. As a result, threading engagement of the set screw 330 along the arm portions 314a, 314b is limited. Specifically, threading advancement of the set screw 330 along the arm portions 314a, 314b is blocked when the terminal or final external thread $340_t$ of the set screw body portion 332 is engaged with the terminal internal thread $311_t$ of the screw head portion 306. Accordingly, a gap (similar to the gap g illustrated in FIG. 4) is provided between the lower end surface 342 of the setscrew 330 and the spinal rod, thereby preventing compression of the lower end surface 342 of the setscrew 330 against the spinal rod to allow for relative axial movement between the spinal rod and the bone screw 300. In other words, movement of the spinal rod is unconstrained relative to the bone screw 300. Once the terminal thread $340_t$ of the set screw 330 is engaged with the terminal internal thread 311t in the screw head portion 306, exerting additional torque onto the setscrew 330 beyond a predetermined level will cause the set screw head portion 336 to be sheared or broken off from the remainder of the setscrew 330.

As indicated above, the intermediate bone anchor 24a engaged to the vertebra $V_4$ is securely clamped to the elongate member 22, thereby substantially preventing relative axial movement between the elongate member 22 and the anchor member 24a. However, the outer bone anchors 24b, 24c that are engaged to the vertebrae $V_1$ and $V_7$, respectively, are not securely clamped to the elongate member 22, thereby allowing for relative axial movement between the elongate member 22 and the anchor members 24b, 24c, which in turn allows for relative axial movement between the vertebrae $V_1$ and $V_7$. Accordingly, as the patient's spinal column grows and the distance between the vertebrae $V_1$ and $V_7$ is increased, the outer anchor members 24b, 24c are allowed to slide along the end portions 22a, 22b of the elongate members 22 (i.e., generally along the sagittal plane), which in turn provides for relatively uninhibited axial movement between the vertebrae $V_1$, $V_4$ and $V_7$ to accommodate for growth of the patient's spinal column.

As should be appreciated, the number and frequency of subsequent surgical procedures required for adjustment of the stabilization system 20 to accommodate for growth of the patient's spinal column can be significantly reduced, if not eliminated. The relatively close fit between the elongate members 22 and the lower surface 116 and side surfaces 118a, 118b of the head portion 106 also provides lateral stabilization and support to the portion of the spinal column being treated. Moreover, due to the configuration and operation of the support system 20, the upper and lower vertebral levels on either side of the intermediate vertebrae $V_4$ do not need to be fused, as required in other prior techniques for treating a spinal curvature. Additionally, correction of the spinal curvature via the support system 20 may be further facilitated by performing apical derotation over the intermediate or central vertebral levels.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected.

What is claimed is:

1. A method for stabilizing at least a portion of the spinal column, comprising:
   providing an elongate support member extending along an axis, providing a plurality of anchor members each including a bone engaging portion and a receiver portion defining a passage configured to receive a portion of the support member, and providing a plurality of coupling members each configured for engagement with the receiver portion of the anchor members;
   anchoring a first of the anchor members to a first vertebra;
   anchoring a second of the anchor members to a second vertebra;
   positioning the support member within the receiver portion of the first anchor member and engaging a first of the coupling members with the receiver portion of the first anchor member and compressing the first coupling member against the support member to thereby substantially prevent axial movement of the support member relative to the first anchor member; and
   positioning the support member within the receiver portion of the second anchor member and engaging a second of the coupling members with the receiver portion of the second anchor member to retain the support member within the passage in the receiver portion of the second anchor member while establishing a gap between an end surface of the second coupling member and the support member to thereby allow substantially unconstrained axial movement of the support member relative to the second anchor member,
   wherein the second coupling member and the receiver portion of the second anchor member include structural features that cooperate to prevent the second coupling member from compressing the support member against the receiver portion of the second anchor member to thereby allow the substantially unconstrained axial movement of the support member relative to the second anchor member, and
   wherein the structural features comprise a shoulder defined by the second coupling member that abuts a corresponding distal end surface defined by the receiver portion of the second anchor member to prevent the second coupling member from compressing the support member against the receiver portion of the second anchor member.

2. The method of claim 1, further comprising:
   anchoring a third of the anchor members to a third vertebra; and
   positioning the support member within the receiver portion of the third anchor member and engaging a third of the coupling members with the receiver portion of the third anchor member to retain the support member within the passage in the receiver portion of the third anchor member while establishing a gap between an end surface of the third coupling member and the support member to thereby allow substantially unconstrained axial movement of the support member relative to the third anchor member.

3. The method of claim 2, further comprising positioning the second and third anchor members on opposite sides of the first anchor member relative to the support member.

4. The method of claim 2, further comprising:
   positioning the second and third anchor members adjacent opposite end portions of the support member; and providing the elongate support member with a length such that the end portions of the support member extend beyond the second and third anchor members.

5. The method of claim 2, wherein the elongate support member is arranged substantially parallel with a sagittal plane extending along the spinal column; and wherein the axial movement of the support member relative to the second anchor member accommodates for growth of the spinal column generally along the sagittal plane.

6. The method of claim 2, wherein the first anchor member is anchored to the first vertebra adjacent the coronal apex of the thoracic curve, the second anchor member is anchored to the second vertebra at least one level above the coronal apex, and the third anchor member is anchored to the third vertebra at least one level below the coronal apex.

7. The method of claim 1, wherein the receiver portion of the second anchor member includes a pair of spaced apart arms at least partially defining the passage and including distal end portions defining an opening therebetween in communication with the passage, the opening sized to transversely receive the support member therethrough and into the passage; and wherein the shoulder of the second coupling member abuts the distal end portions of the arms to prevent the second coupling member from compressing the support member against the receiver portion of the second anchor member.

8. The method of claim 1, wherein the passage in the receiver portion of the second anchor member includes a threaded region, the second coupling member including a threaded body portion threadingly engaged within the threaded region of the passage, the second coupling member including a flange portion sized larger than the threaded body portion to define the shoulder.

9. The method of claim 8, wherein the second coupling member includes a head portion extending from the flange portion and being selectively separable therefrom.

10. The method of claim 1, wherein each of the first and second coupling members comprises a set screw.

11. A method for stabilizing at least a portion of the spinal column, comprising:

providing an elongate support member extending along an axis, providing a plurality of anchor members each including a bone engaging portion and a receiver portion defining a passage configured to receive a portion of the support member, and providing a plurality of coupling members each configured for engagement with the receiver portion of the anchor members;

anchoring a first of the anchor members to a first vertebra;

anchoring a second of the anchor members to a second vertebra;

positioning the support member within the receiver portion of the first anchor member and engaging a first of the coupling members with the receiver portion of the first anchor member and compressing the first coupling member against the support member to thereby substantially prevent axial movement of the support member relative to the first anchor member; and positioning the support member within the receiver portion of the second anchor member and engaging a second of the coupling members with the receiver portion of the second anchor member to retain the support member within the passage in the receiver portion of the second anchor member while establishing a gap between an end surface of the second coupling member and the support member to thereby allow substantially unconstrained axial movement of the support member relative to the second anchor member, wherein the receiver portion of the first and second anchor members each includes a pair of spaced apart arms at least partially defining the passage, distal end portions of the arms defining an opening therebetween in communication with the passage, the opening sized to transversely receive the support member therethrough and into the passage, each of the first and second coupling members at least partially closing off the opening in the receiver portion of corresponding ones of the first and second anchor members to retain the support member within the passage.

12. The method of claim 11, wherein the second coupling member includes a threaded body portion engaged within a threaded region, defined along the passage in the receiver portion of the second anchor member, the threaded region configured to block threading advancement of the second coupling member along the passage to establish the gap between the end surface of the second coupling member and the support member to thereby allow the substantially unconstrained axial movement of the support member relative to the second anchor member.

13. The method of claim 12, wherein the threaded region in the receiver portion of the second anchor member has a thread depth that limits threading advancement of tine second coupling member along the passage to prevent the second coupling member from compressing the support member against the receiver portion of the second anchor member.

14. The method of claim 13, wherein the threaded region in the receiver portion of the second anchor member includes a terminal thread that is axially offset from the support member when the support member is seated within the receiver portion of the second anchor member.

15. The method of claim 11, wherein the second coupling member includes a shoulder that engages the distal end portions of the arms of the second anchor member to prevent the second coupling member from compressing the support member against the receiver portion of the second anchor member.

16. The method of claim 11, wherein each of the first and second coupling members comprises a set screw.

17. A method for stabilizing at least a portion of the spinal column, comprising:

providing an elongate support member extending along an axis, providing a plurality of anchor members each including a bone engaging portion and a receiver portion defining a passage configured to receive a portion of the support member, and providing a plurality of coupling members each configured for engagement with the receiver portion of the anchor members;

anchoring a first of the anchor members to a first vertebra;

anchoring a second of the anchor members to a second vertebra;

positioning the support member within the receiver portion of the first anchor member and engaging a first of the coupling members with the receiver portion of the first anchor member and compressing the first coupling member against the support member to thereby substantially prevent axial movement of the support member relative to the first anchor member; and positioning the support member within the receiver portion of the second anchor member and engaging a second of the coupling members with the receiver portion of the second anchor member to retain the support member within the passage in the receiver portion of the second anchor member while establishing a gap between an end surface of the second coupling member and the support member to thereby allow substantially unconstrained axial movement of the support member relative to the second anchor member, wherein the support member is positionable between the end surface of the second coupling member and an opposing surface of the receiver portion of the second anchor member, the end surface and the opposing surface separated by a distance when the second coupling member is fully engaged with the receiver portion of the second anchor member, the support member having an outer dimension that is less than the distance to establish the gap between the end surface of the second coupling member and the support member to thereby allow the substantially unconstrained axial movement of the support member relative to the second anchor member.

18. The method of claim 17, wherein each of the anchor members comprises a bone screw with the bone engaging portion comprising a threaded shaft portion and the receiver portion comprising a U-shaped head portion, the U-shaped head portion including a pair of spaced apart arms at least partially defining the passage, a portion of the arms including internal threads that define a threaded region of the passage, each of the coupling members including a threaded body portion threadingly engaged within the threaded region of the passage.

19. The method of claim 18, wherein the second coupling member including a flange portion defining a shoulder, the shoulder engaged against distal end portions of the arms of the second anchor member to prevent the second coupling member from compressing the support member against the U-shaped head portion of the second anchor member.

20. The method of claim 17, wherein each of the first and second coupling members comprises a set screw.

* * * * *